(12) United States Patent
Kaplan et al.

(10) Patent No.: US 10,736,943 B2
(45) Date of Patent: Aug. 11, 2020

(54) SILK MICROSPHERES FOR ENCAPSULATION AND CONTROLLED RELEASE

(71) Applicant: TRUSTEES OF TUFTS COLLEGE, Medford, MA (US)

(72) Inventors: David L. Kaplan, Concord, MA (US); Xiaoqin Wang, Winchester, MA (US)

(73) Assignee: Trustees of Tufts College, Medford, MA (US)

(*) Notice: Subject to any disclaimer, the term of this patent is extended or adjusted under 35 U.S.C. 154(b) by 341 days.

(21) Appl. No.: 13/888,605

(22) Filed: May 7, 2013

(65) Prior Publication Data
US 2013/0243866 A1 Sep. 19, 2013

Related U.S. Application Data

(63) Continuation of application No. 12/442,595, filed as application No. PCT/US2007/020789 on Sep. 26, 2007, now abandoned.
(Continued)

(51) Int. Cl.
*A61K 9/16* (2006.01)
*A61K 9/19* (2006.01)
(Continued)

(52) U.S. Cl.
CPC ............... *A61K 38/44* (2013.01); *A61K 9/16* (2013.01); *A61K 9/1658* (2013.01); *A61K 9/5052* (2013.01); *A61K 31/7076* (2013.01); *A61K 47/34* (2013.01); *A61K 47/42* (2013.01); *A61K 9/127* (2013.01); *A61K 9/19* (2013.01)

(58) Field of Classification Search
None
See application file for complete search history.

(56) References Cited

U.S. PATENT DOCUMENTS 4,233,211 A 11/1980 Ohtomo et al.
4,806,355 A 2/1989 Goosen et al.
(Continued)

FOREIGN PATENT DOCUMENTS

WO WO-97/08315 A1 3/1997
WO 2005/123114 12/2005
(Continued)

OTHER PUBLICATIONS

Gobin et al., "Silk fibroin coated liposomes for long-term and target drug delivery", International Journal of Nanomedicine, 1(1), 2006, pp. 81-87.*
(Continued)

*Primary Examiner* — Kevin S Orwig
(74) *Attorney, Agent, or Firm* — Quarles & Brady LLP

(57) ABSTRACT

A method was developed to prepare silk fibroin microspheres using lipid vesicles as templates to efficiently load therapeutic agents in active form for controlled release. The lipids are subsequently removed through the use of a dehydration agent, such as methanol or sodium chloride, resulting in β-sheet structure dominant silk microsphere structures having about 2 μm in diameter. The therapeutic agent can be entrapped in the silk microspheres and used in pharmaceutical formulations for controlled-release treatments.

26 Claims, 12 Drawing Sheets

Related U.S. Application Data

(60) Provisional application No. 60/847,100, filed on Sep. 26, 2006.

(51) Int. Cl.
| | | |
|---|---|---|
| *C07K 14/435* | (2006.01) | |
| *A61K 38/44* | (2006.01) | |
| *A61K 47/42* | (2017.01) | |
| *A61K 47/34* | (2017.01) | |
| *A61K 9/50* | (2006.01) | |
| *A61K 31/7076* | (2006.01) | |
| *A61K 9/127* | (2006.01) | |

(56) References Cited

U.S. PATENT DOCUMENTS

| | | | |
|---|---|---|---|
| 5,015,476 A | 5/1991 | Cochrum et al. | |
| 5,093,489 A | 3/1992 | Diamantoglou | |
| 5,245,012 A | 9/1993 | Lombari et al. | |
| 5,263,992 A | 11/1993 | Guire | |
| 5,270,419 A | 12/1993 | Domb | |
| 5,576,881 A | 11/1996 | Doerr et al. | |
| 5,589,167 A | 12/1996 | Cleland et al. | |
| 5,902,800 A | 5/1999 | Green et al. | |
| 6,127,143 A | 10/2000 | Gunasekaran | |
| 6,245,537 B1 | 6/2001 | Williams et al. | |
| 6,267,776 B1 | 7/2001 | O'Connell | |
| 6,302,848 B1 | 10/2001 | Larson et al. | |
| 6,310,188 B1 | 10/2001 | Mukherjee | |
| 6,325,810 B1 | 12/2001 | Hamilton et al. | |
| 6,337,198 B1 | 1/2002 | Levene et al. | |
| 6,372,244 B1 | 4/2002 | Antanavich et al. | |
| 6,379,690 B2 | 4/2002 | Blanchard et al. | |
| 6,387,413 B1 | 5/2002 | Miyata et al. | |
| 6,395,734 B1 | 5/2002 | Tang et al. | |
| 2003/0099630 A1 | 5/2003 | DiBenedetto et al. | |
| 2006/0024379 A1* | 2/2006 | Brown | A61K 9/0019 424/490 |
| 2006/0147415 A1 | 7/2006 | Mousa et al. | |
| 2010/0028451 A1 | 2/2010 | Kaplan et al. | |
| 2013/0171260 A1 | 7/2013 | Kaplan et al. | |
| 2014/0105978 A1 | 4/2014 | Kaplan et al. | |

FOREIGN PATENT DOCUMENTS

| | | | |
|---|---|---|---|
| WO | 2006/042310 | | 4/2006 |
| WO | WO2006/042310 | * | 4/2006 |

OTHER PUBLICATIONS

Zhou et al. "SilkFibroin: StructuralImplicationsofaRemarkableAminoAcidSequence", Proteins: Structure,Function,and Genetics, 44, 2001, pp. 119-122.*

Matthews, B. W. J. Mol. Biol. (1968), 33; pp. 491-497 (cited solely as evidence to rebut appellants' newly presented argument).*

Wlodawer, A., et al. FEBS J. (ePub Nov. 2007), 275(1); pp. 1-21 (cited solely as evidence to rebut appellants' newly presented argument).*

Hino, T., et al., "Change in secondary structure of silk fibroin during preparation of its microspheres by spray-drying and exposure to humid atmosphere," Journal of Colloid and Interface Science 266, 2003, pp. 68-73.

Wang et al., Biomaterials, 27(36):6064-6082 (2006). "Stem cell-based tissue engineering with silk biomaterials."

Brandl, M., Liposomes as drug carriers: a technological approach, Biotechnol. Annu. Rev., 7:59-85 (2001).

Colletier, J.P. et al., Protein encapsulation in liposomes: efficiency depends on interactions between protein and phospholipid bilayer, BMC Biotechnol., 2:9 (2002).

Gombotz, W.R. and Wee, S., Protein release from alginate matrices, Adv. Drug Deliv. Rev., 31(3):267-285 (1998).

Hofmann, S., et al., Silk fibroin as an organic polymer for controlled drug delivery, Journal of Controlled Release, 111:219-227 (2006).

International Search Report for PCT/US2007/020789, 3 pages (dated Nov. 25, 2008).

Jiang, W. et al., Biodegradable poly(lactic-co-glycolic acid) microparticles for injectable delivery of vaccine antigens, Adv. Drug. Deliv. Rev., 57(3):391-410 (2005).

Li, C. et al., Electrospun Silk-BMP-2 scaffolds for Bone Tissue Engineering, Biomaterials, 27:3115-3124 (2006).

Lucas, F. et al., The silk fibroins, Adv. Protein. Chem., 13:107-242 (1958).

Rouser, G. et al., Two dimensional thin layer chromatographic separation of polar lipids and determination of phospholipids by phosphorus analysis of spots, Lipids, 5(5):494-6 (1970).

Sofia, S. et al., Functionalized silk-based biomaterials for bone formation, Journal of Biomedical Materials Research, 54(1): 139-148 (2001).

Written Opinion for PCT/US2007/020789, 5 pages (dated Nov. 25, 2008).

Zhou, X. and Arthur, G., Improved procedures for the determination of lipid phosphorus by malachite green, J. Lipid Res., 33(8):1233-6 (1992).

Shang, K. et al, Accelerated in vitro Degradation of Optically Clear Low b-sheet Silk Films by Enzyme-Mediated Pretreatment, JAMA Ophthalmol., 131(5): 676, 18 pages (2013).

* cited by examiner

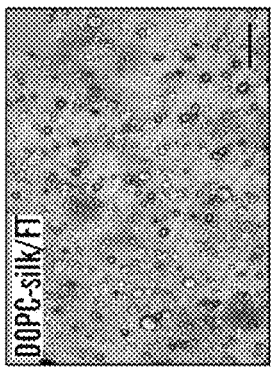
FIG. 1A
FIG. 1B
FIG. 1C
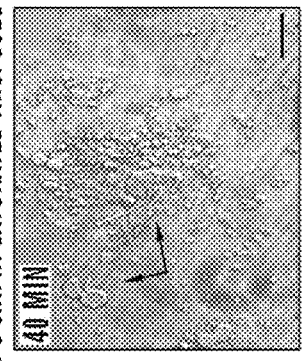
FIG. 1D
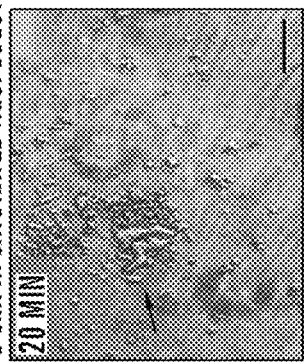
FIG. 1E
FIG. 1F

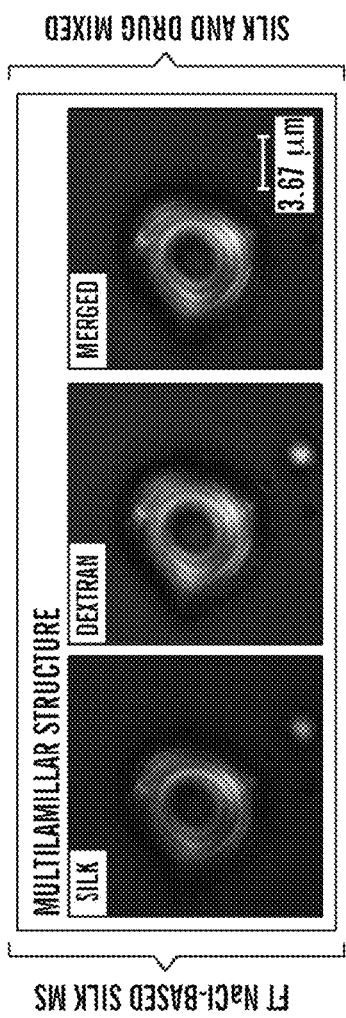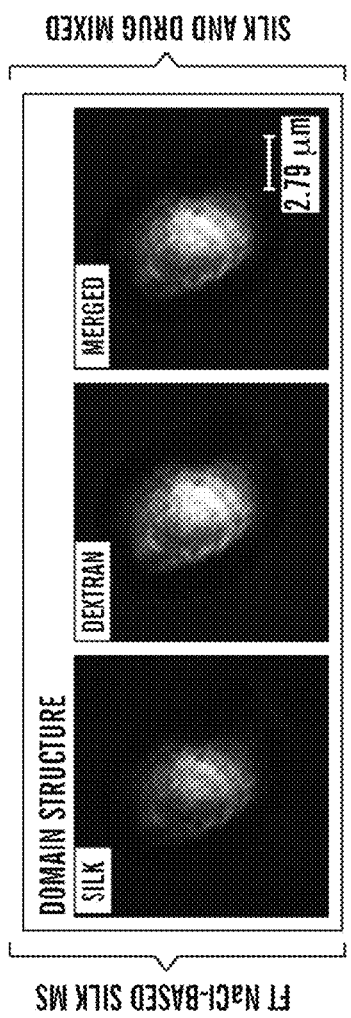
FIG. 6C
FIG. 6D

SILK MICROSPHERES FOR ENCAPSULATION AND CONTROLLED RELEASE

CROSS-REFERENCE TO RELATED APPLICATIONS

This application is a continuation application of U.S. patent application Ser. No. 12/442,595 filed on Jul. 7, 2009, which is a 35 U.S.C. § 371 National Stage Application of International Application No. PCT/US2007/020789 filed on Sep. 26, 2007, which claims benefit under 35 U.S.C. § 119(e) of U.S. Provisional Application No. 60/847,100 filed on Sep. 26, 2006, the contents of each of which are incorporated herein by reference in their entireties.

GOVERNMENT SUPPORT

This invention was made with government support under Grant No. DE016525 awarded by the National Institutes of Health. The Government has certain rights in the invention.

FIELD OF INVENTION

This invention relates to silk fibroin microspheres prepared by mixing silk fibroin with lipids to form microspheres capable of encapsulating therapeutic drugs and releasing the drugs in a controlled manner.

BACKGROUND OF INVENTION

Controlled drug release involves a combination of a polymer matrix with bioactive drugs such that the drugs can be delivered in a predictable manner. Polymeric materials, including biodegradable synthetic polymers such as poly(D, L-lactide-co-glycolide) (PLGA) and natural polymer such as collagen and alginate have been used as drug delivery matrices. These polymer matrices function in many ways as an artificial extracellular matrix (ECM) to stabilize encapsulated proteins, such as growth factors. See Jiang et al., "Biodegradable poly(lactic-o-glycolic acid) microparticles for injectable delivery of vaccine antigens," *Adv. Drug Deliv. Rev.* 57 (2005) 391-410; see also Wee et al., "Protein release from alginate matrices," *Adv. Drug Deliv. Rev.* 31 (1998) 267-285.

The release of encapsulated protein drugs are controlled by both passive diffusion of protein drugs and degradation of polymer matrices. Encapsulation and controlled release are of particular importance for protein drugs with short half-lives when free in solution, and for reduced systemic toxicity. However, preservation of biological activity of incorporated protein drugs in a polymer matrix and control of subsequent release remain major challenges.

Silk fibroin has a long history in clinical applications used as suture threads, and now it is finding new and important applications in the tissue-engineering field as a scaffold support for the growth of artificial tissues such as bone and cartilage. Recently, the use of silk fibroin for controlled drug delivery has been explored with electrospun silk fiber mats that encapsulated bone morphogenetic protein 2 (BMP-2). See Li et al., "Electrospun silk-BMP-2 scaffolds for bone tissue engineering," *Biomaterials* 27 (2006):3115-3124. Hoffman investigated the encapsulation and release of different proteins such as horseradish peroxidase (HRP) and lysozyme from silk films and the correlation between silk crystallinity that were induced by methanol and protein release behaviors. It was found that high silk crystallinity could significantly retard the release of encapsulated proteins. See Hofmann et al., "Silk fibroin as an organic polymer for controlled drug delivery," *J. Control Release* 111 (2006):219-227.

Thus, silk fibroin holds great promise for controlled drug delivery due to its unique structure and crystallinity properties as well as the other advantages discussed above. Silk microspheres can be fabricated using physical methods such as spray-drying, however, harsh conditions such as high temperature have prohibited their uses as a protein drug delivery carrier. See Hino et al., "Change in secondary structure of silk fibroin during preparation of its microspheres by spray-drying and exposure to humid atmosphere," *J. Colloid Interface Sci.* 266 (2003) 68-73. In addition, conventional microspheres typically have a large size (above 100 µm), making them less useful as encapsulation vehicles for many of the smaller drug molecules.

Accordingly, what is needed in the art is a way to prepare silk fibroin microspheres under mild conditions so that protein drugs and other therapeutic agents can be encapsulated in the microspheres and released in their active forms. This invention answers that need.

SUMMARY OF INVENTION

One embodiment of this invention relates to a method of preparing silk fibroin microspheres. The method involves (a) mixing a silk fibroin solution with a lipid composition; (b) lyophilizing the mixture; (c) combining the lyophilized material with a dehydration medium for a sufficient period of time to at least partially dehydrate the silk fibroin solution and induce β-sheet structures in the silk fibroin; and (d) removing at least a portion of the lipids to form silk fibroin microspheres.

Another embodiment of this invention relates to a drug delivery composition comprising a therapeutic agent encapsulated in crosslinked silk fibroin microspheres, wherein the microspheres contain lipid components.

Another embodiment of this invention relates to a method of encapsulating a biomaterial in silk fibroin microcapsules. The method comprises (a) mixing a solution comprising silk fibroin and a biomaterial with a lipid composition; (b) lyophilizing the mixture; (c) combining the lyophilized material with a dehydration medium for a sufficient period of time to at least partially dehydrate the silk fibroin solution and induce β-sheet structures in the silk fibroin; and (d) removing at least a portion of the lipids to produce a biomaterial that has been encapsulated in silk fibroin microspheres.

Another embodiment of this invention relates to a silk fibroin microsphere composition, comprising a therapeutic agent encapsulated in crosslinked silk fibroin microspheres, wherein at least 75% of the microspheres are spherical or substantially spherical, and wherein at least 75% of the microspheres have a diameter ranging from 1.0 to 3.0 µm.

BRIEF DESCRIPTION OF THE FIGURES

FIG. 1 depicts photomicrographs of particle suspensions obtained during silk microsphere preparation of: (A) DOPC film hydrated by water; (B) DOPC film hydrated by silk solution; (C) DOPC-silk mixture after freeze-thaw 3 times; and freeze-thawed and lyophilized DOPC-silk suspended in saturated NaCl solution at 10 min (D), 20 min (E), and 40 min (F). The arrows indicate the fused lipid vesicles. Bar indicates 50 µm.

DETAILED DESCRIPTION

Figure 2A:
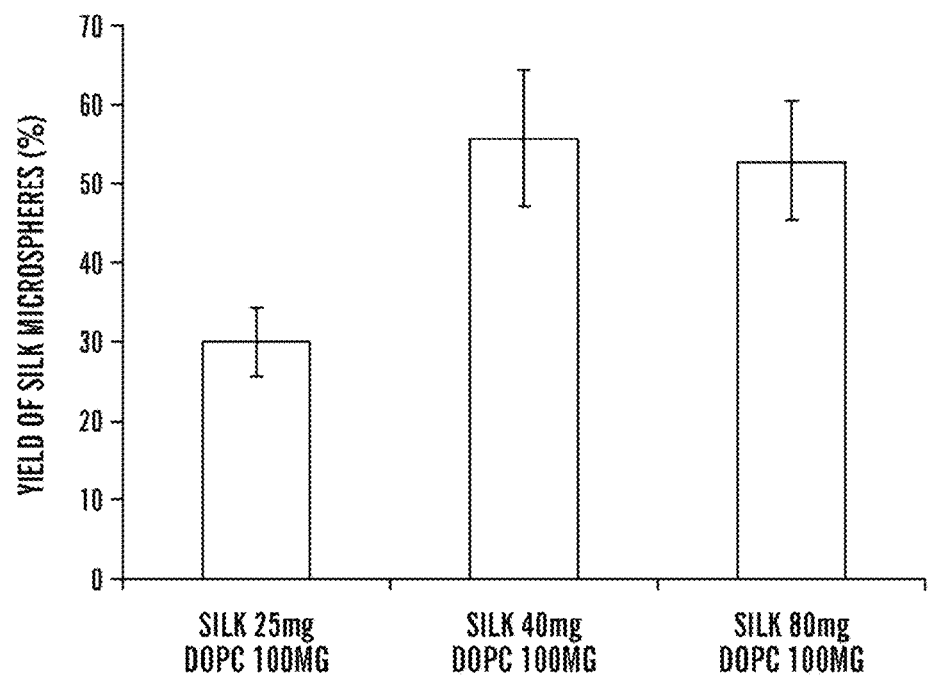
FIG. 2 represents charts depicting the yield of microspheres when (A) silk and DOPC ratio were varied in MeOH-based silk microspheres, and (B) NaCl treatment time was varied in NaCl-based silk microspheres. Error bars represent standard deviations from samples n=3.

This invention relates to a method of preparing silk fibroin microspheres. The method involves (a) mixing a silk fibroin solution with a lipid composition; (b) lyophilizing the mixture; (c) combining the lyophilized material with a dehydration medium for a sufficient period of time to at least partially dehydrate the silk fibroin solution and induce β-sheet structures in the silk fibroin; and (d) removing at least a portion of the lipids to form silk fibroin microspheres.

Silkworm fibroin is the structural protein of silk fibers. Silk fibroin can be fabricated easily into desired shapes, such as films, 3-dimensional porous scaffolds, electrospun fibers, and hydrogels. These materials have the advantage of excellent mechanical properties, biocompatibility and biodegradability. Silk fibroin solutions may be prepared as aqueous stock solution in accordance with the procedures used by Sofia et al., "Functionalized silk-based biomaterials for bone formation," *J. Biomed Mater Res.* 54 (2001) 139-148, herein incorporated by reference in its entirety.

As used herein, the term "fibroin" includes silkworm fibroin and insect or spider silk protein (Lucas et al., *Adv. Protein Chem* 13: 107-242 (1958)). Preferably, fibroin is obtained from a solution containing a dissolved silkworm silk or spider silk. The silkworm silk protein is obtained, for example, from *Bombyx mori*, and the spider silk is obtained from *Nephila clavipes*. In the alternative, suitable silk proteins can be obtained from a solution containing a genetically engineered silk, such as from bacteria, yeast, mammalian cells, transgenic animals or transgenic plants. See, for example, WO 97/08315 and U.S. Pat. No. 5,245,012.

In addition to the silk fibroin, the silk fibroin solution may also contain one or more therapeutic agents. The therapeutic agent may be any agent known by those of skill in the art to have therapeutic properties. Suitable therapeutic agents include proteins, peptides (preferably therapeutic peptides), nucleic acids, PNA, aptamers, antibodies, growth factors, cytokines, enzymes, and small molecules (preferably small medicinal drug compounds having a molecular weight of less than 1000 Da). Preferred therapeutic agents include morphogenetic protein 2 (BMP-2), insulin-like growth factor I and II (IGF-I and II), epidermal growth factor (EGF), platelet-derived growth factor (PDGF), fibroblast growth factors (FGFs), transforming growth factors-β (TGFs-β), transforming growth factors-α, erythropoietin (EPO), interferon α and γ, interleukins, tumor necrosis factor α and β, insulin, antibiotics, and adenosine.

The therapeutic agent, when mixed with the silk fibroin solution, can be encapsulated in the silk fibroin microspheres. The encapsulated therapeutic agent can then be released from the microspheres through typical release mechanisms known in the art. Preferably, the therapeutic agent is in an active form when added to the silk fibroin and in an active form when encapsulated in the silk fibroin microspheres. Keeping the therapeutic agent in an active form throughout the microsphere preparation process enables it to be therapeutically effective upon release from the microsphere.

Biocompatible polymers can also be added to the silk fibroin solution to generate composite matrices. Useful biocompatible polymers include, for example, polyethylene oxide (PEO) (U.S. Pat. No. 6,302,848), polyethylene glycol (PEG) (U.S. Pat. No. 6,395,734), collagen (U.S. Pat. No. 6,127,143), fibronectin (U.S. Pat. No. 5,263,992), keratin (U.S. Pat. No. 6,379,690), polyaspartic acid (U.S. Pat. No. 5,015,476), polylysine (U.S. Pat. No. 4,806,355), alginate (U.S. Pat. No. 6,372,244), chitosan (U.S. Pat. No. 6,310,188), chitin (U.S. Pat. No. 5,093,489), hyaluronic acid (U.S. Pat. No. 6,387,413), pectin (U.S. Pat. No. 6,325,810), polycaprolactone (U.S. Pat. No. 6,337,198), polylactic acid (U.S. Pat. No. 6,267,776), polyglycolic acid (U.S. Pat. No. 5,576,881), polyhydroxyalkanoates (U.S. Pat. No. 6,245,537), dextrans (U.S. Pat. No. 5,902,800), polyanhydrides (U.S. Pat. No. 5,270,419), and combinations thereof (all parenthetical references are to U.S. patent numbers, which illustrate an example of the referenced polymer).

Lipid vesicles are used in the process as templates to assist in modeling the microspheres into preferred shapes and sizes. The lipid composition may include any lipid or combination of lipids that can form liposomes. Suitable lipids in the lipid composition include 1,2-dioleoyl-sn-glycero-3-phosphocholine (DOPC); 1,2-dioleoyl-sn-glycero-3-phophoethanolamine (DOPE); 1,2-dilauroyl-sn-glycero-3-phosphocholine (DLPC); and 1,2-dimyristoyl-sn-glycero-3-phosphocholine (DMPC). Other lipid compositions known in the art may also be used.

The silk fibroin solution and lipid composition should be mixed in a manner that integrates the silk fibroin and lipids. When a therapeutic agent is present in the silk fibroin solution, the therapeutic agent, silk fibroin, and lipids are all mixed together. Preferably, the mixing takes place for a sufficient period of time and under conditions so that the various components are significantly integrated.

Sufficient mixing is sometimes difficult to achieve. In such cases, a freeze-thaw step may be used, which promotes mixing among the lipids, silk fibroin, and therapeutic agents, when present. A freeze-thaw step can break larger multilamellar lipid vesicles into smaller, unilamellar structures that have more homogeneous size distributions. It can also be used to facilitate silk self assembly and enhance the encapsulation of the therapeutic agent in the liposomes.

Any freeze-thaw treatment known in the art may by used. See, e.g., Colletier et al., "Protein encapsulation in liposomes: efficiency depends on interactions between protein and phospholipid bilayer," *BMC Biotechnology* 2 (2002) 9-17, herein incorporated by reference in its entirety, for suitable freeze-thaw techniques. The freeze-thaw may be repeated one or more times to promote further mixing and size homogeneity. Freeze-thawing is not deemed necessary when using certain dehydrating mediums, such as methanol, where the particle-size distribution and integration level achieved through mixing alone is usually adequate.

The amount of silk fibroin solution and lipid composition that is mixed is dependent on the dehydrating medium used and the desired structural formation of the microspheres. Typically, 0.1 to 2 ml of 8 (w/v) % silk solution is used for every 100 mg of lipids. However, these amounts may vary depending on the exact make up of the silk solution and lipid composition. Additionally, depending on the dehydrating medium used, each medium will have a threshold ratio. For instance, when methanol is used as the dehydrating medium, the threshold ratio is 0.2 ml of 8 (w/v) % silk solution for every 100 mg of lipids, and when sodium chloride is used as the dehydrating medium, the threshold ratio is 0.5 ml of 8 (w/v) % silk solution for every 100 mg of lipids. When the amount of lipids are above the threshold ratio, multilamellar structures predominately form in the microspheres; when the amount of lipids are below the threshold ratio, unilamellar structures predominately form in the microspheres.

The lipid components that remain in the microspheres will form as either uni- or multilamellar structures. Compared to multilamellar lipid vesicles, unilamellar vesicles offer higher encapsulation capacity for hydrophilic drugs, more reproducible rates of release, and less lipid content in the microspheres. On the other hand, multilamellar vesicles are suitable for encapsulating both lipophilic and hydrophilic drugs and are more resistant to enzyme digestion, resulting in a longer circulation time in the body. Therefore, unilamellar-structured microspheres are generally preferred when higher drug loading is needed or when hydrophilic drugs are used; multilamellar-structured microspheres are generally preferred when lipophilic drugs are used and in cases when drug loading is not important or when a slower degradation of microspheres is desired. In addition to vesicle structure (uni- or multilamellar), the drug release rate is also governed by lipophilicity of drug molecules, the composition of the encapsulation device, and the lipid composition.

After the silk fibroin solution and the lipid composition have been mixed and optionally freeze-thawed, the mixture is lyophilized. Lyophilization techniques known in the art may be used. Typically, the mixture is lyophilized for three days and stored at temperatures around 4° C.

The lyophilized material is then combined with a dehydration medium. The dehydration medium may be any medium that can both dehydrate the silk fibroin solution and induce β-sheet structures in the silk fibroin. Dehydrating the silk fibroin solution extracts water from the silk fibroin and causes the silk to self assemble and form crystalline β-sheet structures. The β-sheet structures are physical crosslinks in the silk fibroin that provide the silk with stability and unique mechanical features in the fibers. The physical crosslinks also promote the entrapment of therapeutic agents, when present, in the silk fibroin. Beta-sheet structures in the silk fibroin may also be induced by changes in salt concentration and shear forces.

Microspheres will form upon crosslinking of the silk fibroin. Preferably, the weight percentage of microspheres in the total silk is at least about 50%. The amount of microspheres in the silk is dependent on various factors, such as the dehydration agent used to induce β-sheet structure, the type of silk fibroin used, the amount of time the silk is exposed to the dehydration agent, etc. If a therapeutic agent was introduced in the process, then the silk fibroin microspheres can encapsulate the therapeutic agent during microsphere formation.

The dehydration medium should at least partially dehydrate the silk fibroin. Preferably, the silk fibroin is sufficiently dehydrated so that significant amounts (e.g. 50% or more) of β-sheet structures form in the silk. The amount of dehydration time necessary to induce β-sheet formation is readily determinable by one skilled in the art and will depend, in part, on the dehydration medium used. Because high crystallinity can significantly retard the release of encapsulated therapeutic agents, such as proteins, inducing large amounts of β-sheet formation is preferable when forming microspheres designed for control release.

Any known dehydration medium that does not destroy or otherwise damage the silk fibroin may be used as the dehydration medium. Polar alcohols, such as methanol and ethanol, are particularly effective at inducing dehydration of the silk. Other polar solvents, such as acetone, are also effective. Solvents and alcohols with lower polarity, such as chloroform and propanol, may also be used, but are not as effective at stabilizing the silk structure. Additionally, many salts, such as sodium chloride and potassium chloride, can dehydrate the silk fibroin as well change the salt concentration, both of which induce β-sheet formation. Other suitable dehydration mediums include polyethylene glycol solutions, desiccants, and dry gas. Preferably, the dehydration medium is a polar solvent, such as methanol, ethanol, and acetone, or a salt, such as sodium chloride or potassium chloride. Methanol and solutions of sodium chloride are particularly preferred.

The lyophilized material and dehydration medium may be combined through any method known in the art. Preferably, the dehydration medium is in a solution and the lyophilized material is combined with it by adding the lyophilized material to the solution containing the dehydration medium. Combining the two components in this manner will typically form a suspension of the lyophilized material in the dehydration medium solution. When the lyophilized material is suspended in the solution, it allows for easier removal of the lipids.

At least some of the lipids should be removed after the lyophilized material has been combined with the dehydration medium. The lipids may be removed through any technique known in the art. Centrifugation may be used when the lyophilized material is suspended in a solution containing the dehydration medium, however, other removal or extraction techniques may be better suited to remove the lipids depending on the dehydration medium utilized.

Certain dehydration mediums can function to remove the lipids. For instance, a high concentration of methanol or sodium chloride enables each medium to function as both a dehydration medium and lipid remover. Additional removal steps, such as centrifugation, are nonetheless still preferred even when using methanol or sodium chloride. Other dehydration mediums, such as desiccants or dry gas, function little if at all as a lipid remover. These type of dehydration mediums, therefore, may have to be combined with a more rigorous lipid extraction or removal step, or multiple extraction/removal steps.

It is preferable to remove all or substantially all of the removable lipids. Depending on the removal techniques and dehydration medium used, complete lipid removal may not be possible. For instance, when using methanol as the dehydration medium, about 99% of the lipids are able to be removed; when using sodium chloride as the dehydration medium, about 83% of the lipids are able to be removed. In these cases, all or substantially all of the removable lipids are considered to have been removed because further removal techniques would not lead to any substantial amount of additional lipids being removed.

While it is preferable to remove most of the lipids, it is also believed that the lipid components, when present in a relatively small amount, can be beneficial. In particular, it is believed that the lipid component can assist in controlling the release of the therapeutic agent from the microspheres. Therefore, according to an embodiment of the invention, it is preferable to have a microsphere composition where about 15 to about 20% of the total lipids remain in the silk fibroin microspheres. It is also preferable to have a microsphere composition where less than about 5% of the total lipids remain in the silk fibroin microspheres. More preferably, less than about 2% of the total lipids remain in the microspheres.

After the desired amount of lipids have been removed, the composition is typically in a dehydrated pellet form. The composition may be hydrated by suspending or resuspending the microsphere composition in water or a buffer solution. Suspending the microspheres in water or a buffer is often done before the microsphere composition is used in a commercially viable manner. For instance, if the silk fibroin microspheres are used in a formulation suitable for administration, the formulation will typically contain hydrated microspheres.

A pharmaceutical formulation may be prepared that contains the silk fibroin microspheres having encapsulated therapeutic agents. The formulation can be administered to a patient in need of the particular therapeutic agent that has been encapsulated in the microspheres.

The pharmaceutical formulation may be administered by a variety of routes known in the art including topical, oral, parenteral (including intravenous, intraperitoneal, intramuscular and subcutaneous injection as well as intranasal or inhalation administration) and implantation. The delivery may be systemic, regional, or local. Additionally, the delivery may be intrathecal, e.g., for CNS delivery.

In addition to the silk microspheres, the pharmaceutical formulation may also contain a targeting ligand. Targeting ligand refers to any material or substance which may promote targeting of the pharmaceutical formulation to tissues and/or receptors in vivo and/or in vitro with the formulations of the present invention. The targeting ligand may be synthetic, semi-synthetic, or naturally-occurring. Materials or substances which may serve as targeting ligands include, for example, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, and genetic material, including nucleosides, nucleotides, nucleotide acid constructs, peptide nucleic acids (PNA), aptamers, and polynucleotides. Other targeting ligands in the present invention include cell adhesion molecules (CAM), among which are, for example, cytokines, integrins, cadherins, immunoglobulins and selectin.

The pharmaceutical formulations may also encompass precursor targeting ligands. A precursor to a targeting ligand refers to any material or substance which may be converted to a targeting ligand. Such conversion may involve, for example, anchoring a precursor to a targeting ligand. Exemplary targeting precursor moieties include maleimide groups, disulfide groups, such as ortho-pyridyl disulfide, vinylsulfone groups, azide groups, and iodo acetyl groups.

The pharmaceutical formulations may contain common components found in other pharmaceutical formulations, such as known excipients. Exemplary excipients include diluents, solvents, buffers, solubilizers, suspending agents, viscosity controlling agents, binders, lubricants, surfactants, preservatives and stabilizers. The formulations may also include bulking agents, chelating agents, and antioxidants. Where parenteral formulations are used, the formulation may additionally or alternately include sugars, amino acids, or electrolytes.

Suitable excipients include polyols, for example, of a molecular weight less than about 70,000 kD, such as trehalose, mannitol, and polyethylene glycol. See for example, U.S. Pat. No. 5,589,167, the disclosure of which is incorporated by reference herein. Exemplary surfactants include nonionic surfactants, such as Tweeng surfactants, polysorbates, such as polysorbate 20 or 80, etc., and the poloxamers, such as poloxamer 184 or 188, Pluronic polyols, and other ethylene/polypropylene block polymers, etc. Suitable buffers include Tris, citrate, succinate, acetate, or histidine buffers. Suitable preservatives include phenol, benzyl alcohol, metacresol, methyl paraben, propyl paraben, benzalconium chloride, and benzethonium chloride. Other additives include carboxymethylcellulose, dextran, and gelatin. Suitable stabilizing agents include heparin, pentosan polysulfate and other heparinoids, and divalent cations such as magnesium and zinc.

The pharmaceutical formulations containing the microspheres can be administered in a controlled-release manner so that portions of the therapeutic agent are released in the patient over a period of time. The therapeutic agent may release quickly or slowly. For instance, the pharmaceutical formulation can be administered so that less than about 5% of the therapeutic agent is released in the patient from the microspheres over a period of one month. Alternatively, a larger portion of the therapeutic agent may be released initially, with a smaller portion retained in the microspheres and released later. For example, the pharmaceutical formulation can be administered so that at least 5% of the therapeutic agent remains in the microspheres 10 days after administration.

When administering the therapeutic agent in a controlled-release manner, the therapeutic agent preferably remains active in the microspheres so that it can perform its therapeutic function upon release. Certain therapeutic agents become inactive when exposed to encapsulation conditions for a significant period time. Of course, the release of inactive therapeutic agents is of little or no value to the patient, who is not able to receive the benefits of an active therapeutic agent. A preferred pharmaceutical formulation contains microspheres where the activity of the therapeutic agent in the microspheres remains at at least 50% one month after administration to the patient.

Controlled release permits dosages to be administered over time, with controlled release kinetics. In some instances, delivery of the therapeutic agent is continuous to the site where treatment is needed, for example, over several weeks. Controlled release over time, for example, over several days or weeks, or longer, permits continuous delivery of the therapeutic agent to obtain preferred treatments. The controlled delivery vehicle is advantageous because it protects the therapeutic agent from degradation in vivo in body fluids and tissue, for example, by proteases.

Controlled release from the pharmaceutical formulation may be designed to occur over time, for example, for greater than about 12 or 24 hours. The time of release may be selected, for example, to occur over a time period of about 12 hours to 24 hours; about 12 hours to 42 hours; or, e.g., about 12 to 72 hours. In another embodiment, release may occur for example on the order of about 2 to 90 days, for example, about 3 to 60 days. In one embodiment, the therapeutic agent is delivered locally over a time period of about 7-21 days, or about 3 to 10 days. In other instances, the therapeutic agent is administered over 1, 2, 3 or more weeks in a controlled dosage. The controlled release time may be selected based on the condition treated. For example, longer times may be more effective for wound healing, whereas shorter delivery times may be more useful for some cardiovascular applications.

Another embodiment of this invention relates to a drug delivery composition comprising a therapeutic agent encapsulated in crosslinked silk fibroin microspheres, wherein the microspheres contain lipid components. The silk fibroin microspheres may be crosslinked by exposing the silk fibroin to a dehydrating medium, such as methanol or sodium chloride, which induces β-sheet formation, or the crosslinking of the silk fibroin.

When silk fibroin microspheres are prepared with a process that utilizes lipid components, a portion of the lipid components is typically present in the silk fibroin microspheres, even when all of the removable lipid components have been removed. Depending on the process used to incorporate and/or remove the lipids, lipid components will typically be present in the microspheres from about 1 to about 25%, by weight. Preferably, the microspheres contain less than about 20% lipids by weight, more preferably less than about 5% lipids by weight. It is believed that the lipids, when present in relatively small amounts, assist in controlling the release of the therapeutic agent from the microspheres. When the microspheres contain too high a percentage of lipids, the structure and physical parameters of the silk fibroin microspheres can be compromised, resulting in less effective microspheres or microspheres with insufficient structural integrity.

Another embodiment of this invention relates to a method of encapsulating a biomaterial in silk fibroin microcapsules. The method comprises (a) mixing a solution comprising silk fibroin and a biomaterial with a lipid composition; (b) lyophilizing the mixture; (c) combining the lyophilized material with a dehydration medium for a sufficient period of time to at least partially dehydrate the silk fibroin solution and induce β-sheet structures in the silk fibroin; and (d) removing at least a portion of the lipids to produce a biomaterial that has been encapsulated in silk fibroin microspheres.

The biomaterial may be a therapeutic agent, such one or more of the therapeutic agents discussed above. However, the encapsulation process does not have to be used in the field of pharmaceutical formulations and controlled-release methods. The silk fibroin microcapsules may encapsulate various other biomaterials useful in a variety of fields. For instance, the biomaterial may be an enzyme or an enzyme-based electrode. The enzyme or enzyme-based electrode may be used in the field of tissue engineering, biosensors, the food industry, environmental control, or biomedical applications. The system can also be used as a reservoir for a variety of needs, such as in the food industry to harbor vitamins, nutrients, antioxidants and other additives; in the environmental field to harbor microorganisms for remediation or water treatments; in materials as additives to serve as a source of in situ detection and repair components, such as for nondestructive evaluation of material failures and self-repairs of the materials; and for biodetection schemes to help stabilize cells, molecules and related systems.

The silk fibroin microspheres of the invention form in a manner that provides them with advantageous physical properties that are particularly useful for encapsulating therapeutic agents for uses in controlled-release pharmaceutical formulations. The microspheres exhibit a more homogeneous shape and size, especially when compared to microspheres prepared via conventional techniques, such as spray-dry methods. Exhibiting a homogeneous spherical shape, the microspheres are less likely to experience aggregation, which occurs more commonly when the microspheres are in a funicular (fibrillar or elongated) state. The smaller and more narrow diameter range of microspheres also provides a more consistent and controlled release.

Accordingly, an embodiment of this invention relates to a silk fibroin microsphere composition, comprising a therapeutic agent encapsulated in crosslinked silk fibroin microspheres, wherein at least 75% of the microspheres are spherical or substantially spherical, and wherein at least 75% of the microspheres have a diameter ranging from about 1.0 to about 3.0 µm. Preferably, at least 90% of the microspheres are spherical or substantially spherical, and at least 90% of the microspheres have a diameter ranging from about 1.0 to about 3.0 µm. More preferably, at least 95% of the microspheres have a diameter ranging from about 1.0 to about 3.0 µm. The average size of the microspheres is preferably less than about 2.0 µm. The silk microspheres with small sizes are of more interest for biomedical applications.

Figure 3D:
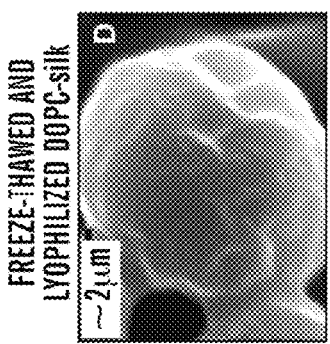
FIG. 3 depicts SEM images of freeze-thawed and lyophilized DOPC-silk silk microspheres when untreated (A-D), treated with methanol (E-H), and treated with NaCl for 15 h (I-L). Bar indicates 20 µm in A, E, I; 5 µm in B, F, J; and 2 µm in C, D, G, H, K, and L.
Figure 3C:
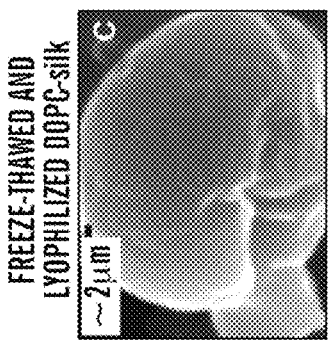
Figure 3B:
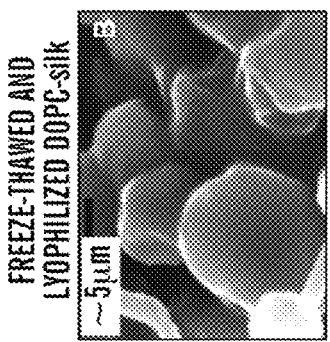
Figure 3A:
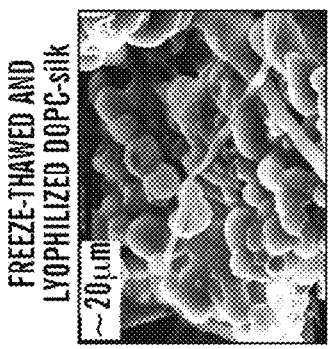
Figures 3E, 3F, 3G, 3H:
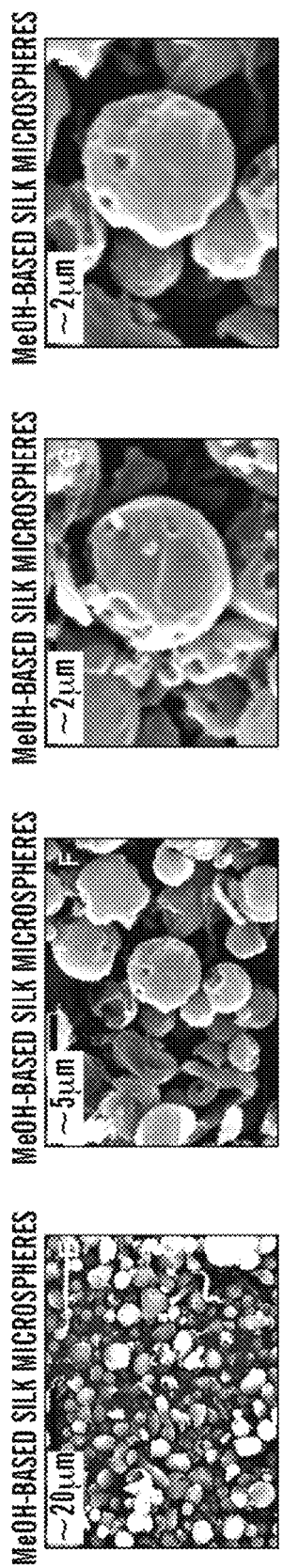
Figures 3I, 3J, 3K, 3L:
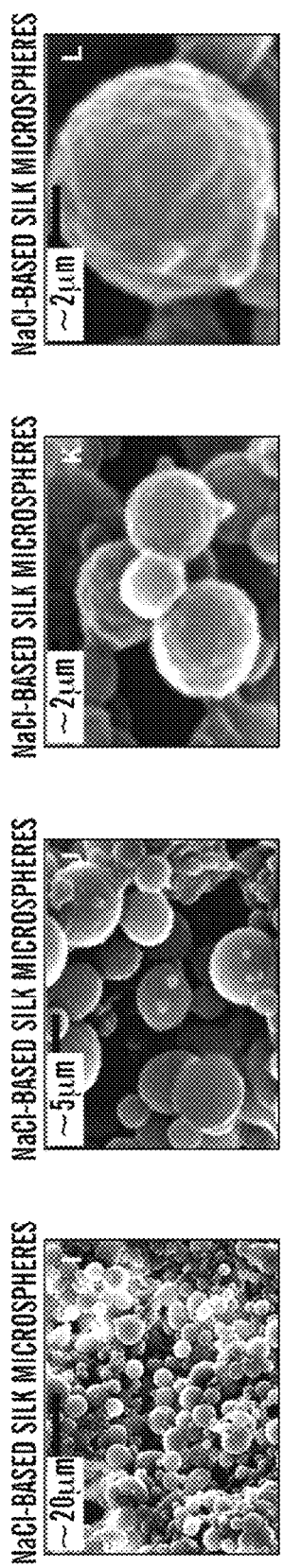

The size and shape of the microsphere will be dependent, to some degree, on what techniques are used to crosslink the silk fibroin. For instance, dehydrating the silk fibroin in methanol in the above-described methods will typically produce microspheres wherein about 90% of the microspheres are substantially spherical and about 90% have a diameter ranging from 1.0 to 3.0 µm. The term "substantially spherical," as used herein, means spherical microspheres that contain small blemishes in the surface or on the edges of the microspheres, but that would otherwise be considered spherical as opposed to funicular. See FIG. 3E, depicting substantially spherical microspheres. Using these methods with sodium chloride will typically produce microspheres wherein about 90% of the microspheres are spherical and about 98% have a diameter ranging from 1.0 to 3.0 µm. See FIG. 3I, depicting spherical microspheres.

Unless otherwise defined, all technical and scientific terms used herein have the same meaning as commonly understood by one of ordinary skill in the art. Although methods and materials similar or equivalent to those described herein can be used in the practice or testing of the invention, the preferred methods and materials are described below. All publications, patent applications, patents and other references mentioned herein are incorporated by reference. In addition, the materials, methods and examples are illustrative only and not intended to be limiting. In case of conflict, the present specification, including definitions, controls.

The invention will be further characterized by the following examples which are intended to be exemplary of the invention.

EXAMPLES

Materials:

Cocoons of *B. mori* silkworm silk were supplied by M. Tsukada (Institute of Sericulture, Tsukuba, Japan). 1,2-Dioleoyl-sn-glycero-3-phosphocholine (DOPC) and 1,2-dioleoyl-sn-glycero-3-phosphoethanolamine-N-(carboxyfluorescein) (fluorescein-DOPE) were purchased from Avanti Polar Lipids (Alabaster, Ala.). 5-(Aminoacetamido) fluorescein (fluoresceinyl glycine amide) was purchased from Molecular Probes (Carlsbad, Calif.). Rhodamine B isothiocyanate-Dextran (M.W. 40,000 Da), horseradish peroxidase (HRP), β-galactosidase, and other chemicals were obtained from Sigma Aldrich (St. Louis, Mo.). 3,3'5,5' Tetramethylbenzidine (TMB) solution was purchased from BioFX laboratories (Owing Mills, Md.). 1-Ethyl-3-[3-dimethylaminopropyl]carbodiimide hydrochloride (EDC), N-hydroxysuccinimide NHS), and hydroxylamine hydrochloride were purchased from Pierce Biotechnology (Rockford, Ill.). All other chemicals were purchased from Sigma-Aldrich (St. Louis, Mo.).

Purification and Fluorescent Labeling of Silk Fibroin:

Silk fibroin aqueous stock solutions were prepared as described by Brandl, "Liposomes as drug carriers: a technological approach," *Biotechnol. Ann. Rev.* 7 (2001) 59-85, herein incorporated by reference in its entirety. Briefly, cocoons of *B. mori* were boiled for 20 min in an aqueous solution of 0.02 M sodium carbonate, and then rinsed thoroughly with pure water. After drying, the extracted silk fibroin was dissolved in 9.3 M LiBr solution at 60° C. for 4 hours, yielding a 20% (w/v) solution. This solution was dialyzed against distilled water using Slide-a-Lyzer dialysis cassettes (MWCO 3,500, Pierce) for 3 days to remove the salt. The solution was clear after dialysis and was centrifuged to remove silk aggregates (small amount) that formed during the dialysis and some dirt from cocoons. The final concentration of silk fibroin aqueous solution was approximately 8% (w/v). This concentration was determined by weighing the residual solid of a known volume of solution after drying.

For fluorescent labeling, the silk fibroin stock solution was diluted to 2% (w/v) with water, and 10 ml of the diluted solution was dialyzed against 500 ml of 0.1 M 2-(morpholino)ethanesulfonic acid (MES) solution (pH 5.6) (Pierce, Chemicals, IL) supplemented with 0.9% NaCl overnight. Eighty mg EDC (2 mM) and 220 mg NHS (5 mM) were added to the buffered silk solution with stirring and the reaction was continued for 15 min. β-mercaptoethanol was added to a final concentration of 20 mM to quench the unreacted EDC. The carboxyl groups on silk fibroin were activated for reacting with primary amines. After the reaction, 10 mg of fluoresceinyl glycine amide was added to the solution so that the molar ratio between fluorescent probe and silk fibroin was about 40:1. The coupling reaction went for 2 hours under slow stirring at room temperature and then 8 mg hydroxylamine hydrochloride was added to quench the reaction. Finally the solution was dialyzed exhaustively against water. The final concentration of fluorescent silk fibroin was approximately 1.5% (w/v) using the same weighing method.

Preparation of Silk Microspheres:

One hundred mg of DOPC was dissolved in 1 ml chloroform in a glass tube and dried into a film under a flow of nitrogen gas. 8% (w/v) silk fibroin solution with volume of 0.33 ml, 0.5 ml, and 1 ml was added to hydrate the lipid film, and the mixture was diluted to 2 ml with water and moved to a plastic tube. The sample was frozen in liquid nitrogen for 15 min and then thawed at 37° C. for 15 min. This freeze-thaw cycle was repeated 3 times and then the thawed solution was slowly pipetted into a glass beaker containing 50 ml water with fast stirring. For methanol-treated microspheres, the freeze-thaw treatment was skipped and the 0.5 ml of DOPC-silk mixture was diluted to 50 ml water directly. The resulting solution was lyophilized for 3 days and stored at 4° C.

To prepare MeOH-based microspheres, 20 mg lyophilized material was suspended in 2 ml MeOH in an Eppendorf tube and the suspension was incubated for 30 min at room temperature followed by centrifugation at 10,000 rpm for 5 min at 4° C. (Eppendorf 5417R centrifuge). The pellet obtained was dried in air and stored at 4° C. To generate a suspension of silk microspheres, the dried pellet was washed once with 2 ml of water by centrifugation, and then resuspended in the desired water or buffer. The clustered microspheres were dispersed by ultrasonication for 10 sec at 30% amplitude (approximately 20 W) using a Branson 450 ultrasonicator (Branson Ultrasonics Co., Danbury, Conn.).

To prepare NaCl-based microspheres, 20 mg lyophilized material was suspended in 2 ml saturated NaCl solution in an Eppendorf tube and the suspension was incubated at room temperature for 1 h, 4 h, and 15 h followed by centrifugation at 10,000 rpm for 5 min at 4° C. (Eppendorf 5417R centrifuge). The supernatant and the white viscous material floating on the top were carefully removed, and the pellet was washed once with 2 ml water by centrifugation and then resuspended in water or buffer.

Phospholipids Quantification

Phospholipids remained in the silk microspheres and were estimated by phosphorus determination through an acidic digestion. See Rouser et al., "Two dimensional then layer chromatographic separation of polar lipids and determination of phospholipids by phosphorus analysis of spots," *Lipids* 5 (1970):494-496, and Zhou et al., "Improved procedures for the determination of lipid phosphorus by malachite green," *J. Lipid Res.* 33 (1992):1233-1236, both of which are herein incorporated by reference in their entirety. The released phosphorus was reacted with ammonium molybdate to form a strong blue color.

Dried MeOH-based and NaCl-based silk microspheres were weighed and transferred into clean glass tubes. 0.65 ml perchloric acid was added to each sample, and the tubes were heated at 180° C. until the yellow color in all the tubes disappeared. When cool, the tubes were supplemented with 3.3 ml water, 0.5 ml 2.5% (w/v) molybdate solution and 0.5 ml 10% (w/v) ascorbic acid solution. The tubes were agitated on a vortex after each addition. The samples were then boiled in a water bath for 5 min, and the absorbance of cool samples (including the standards) was read at 800 nm. Potassium phosphate monobasic ($KH_2PO_4$) solution was used as a standard. The stock solution of 439 mg per liter water (i.e., 100 μg phosphorus per milliliter water) was diluted in 3.3 ml water and 0.65 ml perchloric acid. Digestion at 180° C. was not necessary before adding reagents. The amount of phospholipids was calculated directly on a weight basis after multiplying the amount of phosphorus by 25.38 (DOPC contains 3.94% w/w phosphorus).

Dynamic Light Scattering (DLS)

Microspheres were diluted in 10 ml water in a glass vial and analyzed immediately at 25° C. using a BIC BI-200 SM research goniometer and laser light scattering system (Brookhaven Instrument, Holtsville, N.Y.). Laser light at 532 nm was used to measure the fluctuation in intensity of light scattered by particles. Data were collected for 5 min for each sample, and the mean diameter of particles was calculated using the BIC dynamic light scattering software supplied by the manufacturer of the above-referenced system.

Fourier Transform Infrared (FTIR) Spectroscopy

FTIR studies were performed using a Bruker Equinox 55 FTIR spectrometer. A drop of microsphere suspension was added to the zinc selenide (ZnSe) crystal cell and examined with the FTIR microscope in the reflection mode. Background measurements were taken with an empty cell and subtracted from the sample reading. DOPC suspended in water did not show peaks at the amide I band region, meaning that its influence was negligible. Deconvolution of the fibroin amide I spectra was performed using Gaussian× Lorentzian function in the spectroscopic software from Briler (version 4.2). The curves that had absorption bands at the frequency range of 1620-1630 $cm^{-1}$ and 1695-1700 $cm^{-1}$ represented enriched β-sheet structure in silk II form (23). The contribution of these curves (β-sheet structure content) to the amide I band was assessed by integrating the area under the curve and then normalizing to the total area under the amide I band region (1600-1700 $cm^{-1}$).

Scanning Electron Microscopy (SEM)

For lyophilized DOPC-silk and MeOH-based microspheres, dried materials were directly mounted on samples mounts. For NaCl-based microspheres, the solution containing microspheres were dried on plastic slides which were further cut and mounted. Specimens were then sputter-coated with Au using a Ploaron SC502 Sputter Coater (Fison Instruments, UK), and examined using a JEOL JSM 840A Scanning Electron Microscope (Peabody, Mass.) at 15 KV.

Phase Contrast and Confocal Laser Scanning Microscopy

Microspheres were suspended in pure water and approximately 20 μl of suspension was put on a glass slide and covered with a cover-slip. The samples were analyzed by a phase contrast light microscope (Carl Zeiss, Jena, Germany) equipped with a Sony Exwave HAD 3CCD color video camera, or a confocal laser scanning microscope (TCS Leica SP2, Welzlar, Germany) with Leica Confocal Software, version 2.5 (Leica Microsystems, Heidelberg, Germany).

HRP Loading and Release

Silk microspheres were prepared as described above except that 10 μl of rhodamine B-labeled dextran, 40,000 Da or HRP stock solution at 12.5 mg/ml in buffer, were mixed with 0.5 ml of 8% (w/v) silk solution prior to microsphere formation. Dulbecco's phosphate buffer, pH 7.2 (Invitrogen, Carlsbad, Calif.) was used for all HRP determinations. For loading and release, 40 mg of lyophilized DOPC-silk fibroin was treated with MeOH or NaCl as described. After washing with buffer, the microspheres were suspended in 2 ml of phosphate buffer, pH 7.2. One ml aliquots of the suspension were used for HRP loading, and the other 1 ml aliquot for HRP release. TMB (HRP substrate, Mw=240 Da) was oxidized during the enzymatic degradation of $H_2O_2$ by HRP. The oxidized product of TMB exhibited a deep blue color which turned to yellow upon addition of the acidic stop solution.

For loading determinations, 5 μl of the suspension was mixed with 100 μl of TMB solution in 96-well standard microplate wells for 1 min at room temperature. The reaction was stopped by the addition of 100 μl 0.1 M sulfuric acid. Absorbance was detected at 450 nm by using a VersaMax microplate reader (Molecular devices, Sunnyvale, Calif.). The HRP content was obtained using a HRP standard curve generated under the same condition. The remaining microspheres (995 μl) were spun down, dried and weighed. The loading was obtained as follows:

$$\text{Loading } (\mu g/mg) = \frac{HRP \text{ content } (\mu g) \times 199}{\text{Weight of microspheres (mg)}}$$

The loading efficiency was calculated as follows:

$$\text{Loading efficiency } (\%) = \frac{HRP \text{ loading } (\mu g/mg) \times \text{Total microspheres (mg)}}{\text{Total } HRP (\mu g)}$$

To determine HRP release, 1 ml suspensions of silk microspheres were incubated at room temperature. At desired time points, the suspensions were centrifuged at 10,000 rpm for 2 min. The supernatant was carefully moved to another tube and the pellet was resuspended in 1 ml fresh buffer. HRP content in the supernatant was determined as described above and the percentage of release was obtained by comparing this data with the loading data. All experiments were performed in triplicate. Statistical analysis of data was performed using the Student's t-test. Differences were considered significant when p<0.05.

Liposome-Assisted Silk Microsphere Preparation

FIG. 1 shows the microscopic images of particle suspensions that were generated in the different steps. As a control, hydration of the DOPC film with water resulted in highly dispersed vesicles with a heterogeneous size distribution (FIG. 1A). Hydration of DOPC films with silk fibroin solution resulted in clustered vesicles with similar heterogeneous size distributions (FIG. 1B). Once the DOPC-silk mixture was freeze-thawed 3 times, the water suspension was dominated by highly dispersed particles with a homogeneous size distribution (FIG. 1C). Once the freeze-thawed and lyophilized DOPC-silk was suspended in saturated NaCl solution, some particles fused in time into larger lipid vesicles (FIGS. 1D-E). During preparation, these larger lipid vesicles floated on top of the NaCl solution and could be removed by subsequent centrifugation. The reason that some vesicles tend to fuse in this case is probably due to high lipid content within the vesicles. Those with low lipid but high silk content could survive and be treated into solid NaCl-based microspheres that were precipitated by centrifugation. Similarly, MeOH dissolved those lipid-rich vesicles but treated those silk-rich vesicles into MeOH-based microspheres.

Yield of Silk Microspheres

Figure 2B:
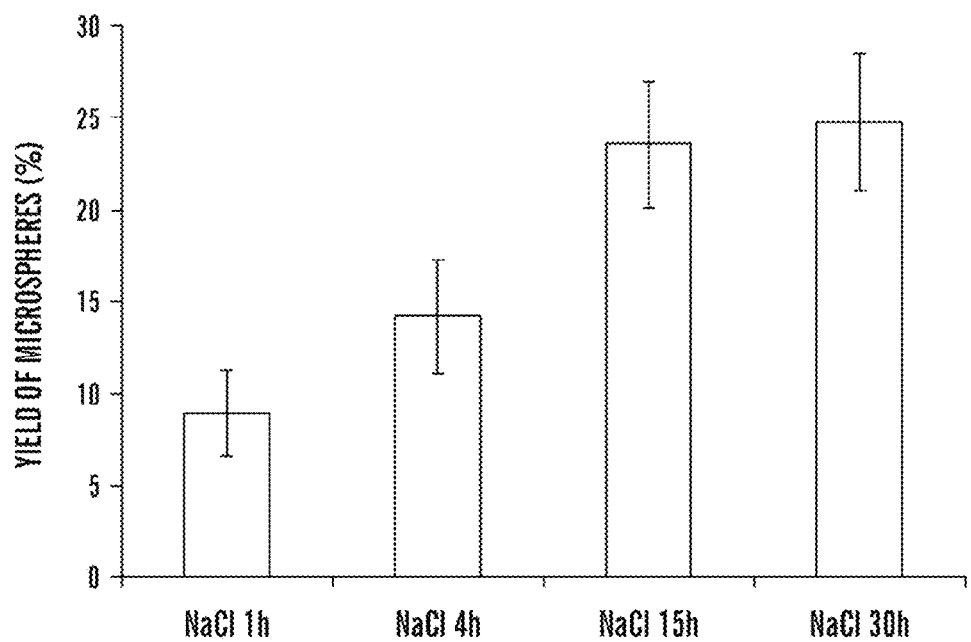

The lipid-to-silk ratio was adjusted to obtain a high yield of microspheres (the weight percentage of microspheres in the total silk). In this example, MeOH treatment was used, and the weights of microspheres were compared with the total silk that was originally added. As shown in FIG. 2A, a yield of about 55% was obtained when 40 mg of silk (0.5 ml 8% w/v silk solution) was mixed with 100 mg DOPC. Silk was encapsulated to a saturated level in the lipid vesicles at this ratio but it was diluted when below the ratio and, therefore, was easier to be dispersed by MeOH. Thus, 0.5 ml 8% w/v silk solution and 100 mg DOPC was used as a standard condition for other preparations. Thirty-minute treatment time was used to prepare MeOH-based microspheres, which was found to be sufficient to induce characteristic silk II β-sheet structures. For NaCl-based preparations, the yields were reported in FIG. 2B. The yield of microspheres was significantly increased with NaCl treatment time, indicating that long NaCl treatment time (at least 15 h) is preferred for lipid removal and silk self-assembly, which is consistent with the observation by microscopic study (FIG. 1) and FTIR study (FIG. 3).

Particle Sizes

MeOH-based microspheres had an average size of 1.7 μm, as determined by dynamic light scattering (Table 1). The average size of NaCl-based microspheres decreased with time of NaCl treatment, from 2.7 μm for 1 hour to 1.6 μm when treated for 15 hours (Table 1), indicating that the silk microspheres became more condensed upon NaCl-treatment.

As shown in FIGS. 3 E-H, approximately 90% of the methanol-based microspheres have a particle size ranging from 1.0 μm to 3.0 μm. As shown in FIGS. 3 I-L, approximately 98% of the sodium chloride-based microspheres have a particle size ranging from 1.0 μm to 3.0 μm.

Phospholipid Content

The phospholipids contents remained in the silk microspheres were determined by phosphorus assay as described in the materials and methods. The result showed that the MeOH-based and NaCl-based microspheres contained about 1% w/w and 17% w/w DOPC, respectively (Table 1).

Surface Morphology

The lyophilized DOPC-silk microspheres showed a smooth surface by SEM (FIG. 3, A-D). A similar surface morphology was observed for the NaCl-treated microspheres (FIG. 3, I-L). The MeOH-based microspheres exhibited a rougher surface that displayed minor defects at the sub-micron level (FIG. 3, E-H). It is believed that the difference in surface morphology between MeOH- and NaCl-based microspheres might have reflected their difference in phospholipids contents.

As shown in FIGS. 3 E-H, approximately 90% of the methanol-based microspheres have a substantially spherical shape. As shown in FIGS. 3 I-L, approximately 90% of the sodium chloride-based microspheres have a spherical shape.

Lamellar Structures

Figure 4A:
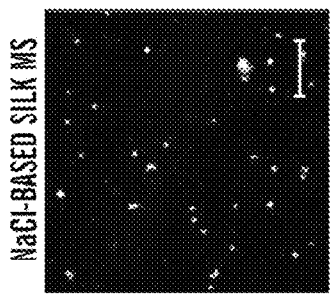
FIG. 4 depicts confocal laser scanning microscopy images of the silk microspheres containing fluorescein-labeled DOPE. Labeled phospholipids remained in MeOH-based silk microspheres (A) and NaCl-based silk microspheres (B), forming either multilamellar structures (C) or non-lamellar structure (D). Bar indicates 75 µm in A and B; 7.36 µm in C; and 10.77 µm in D.
Figure 4B:
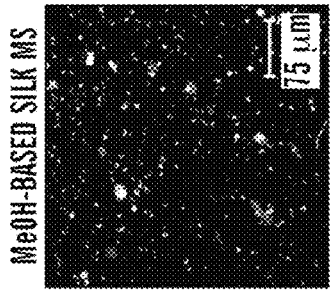
Figure 4C:
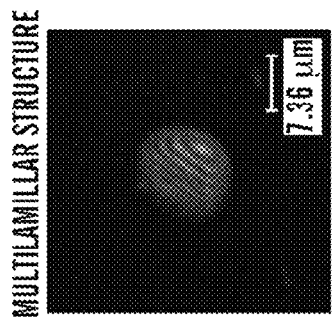
Figure 4D:
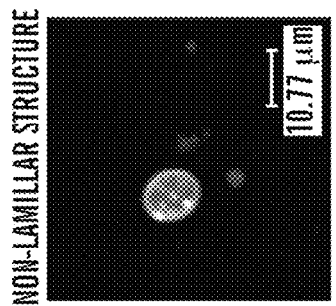

Fluorescent probe (fluorescein)-labeled DOPE was used to trace the phospholipids remaining in the microspheres using confocal laser scanning microscopy. Phospholipids remained in the MeOH- and NaCl-based silk microspheres (FIGS. 4A and B), forming either multilamellar (FIG. 4C) or unilamellar structures (FIG. 4D). The formation of lamellar structure is believed to be influenced by the ratio between lipid and silk in a microsphere: Once the ratio is above a critical level, lipid will dominate the formation of multilamellar structures, while below this level the silk fibroin would dominate the formation of unilamellar structures.

Silk β-Sheet Structures

Figure 5:
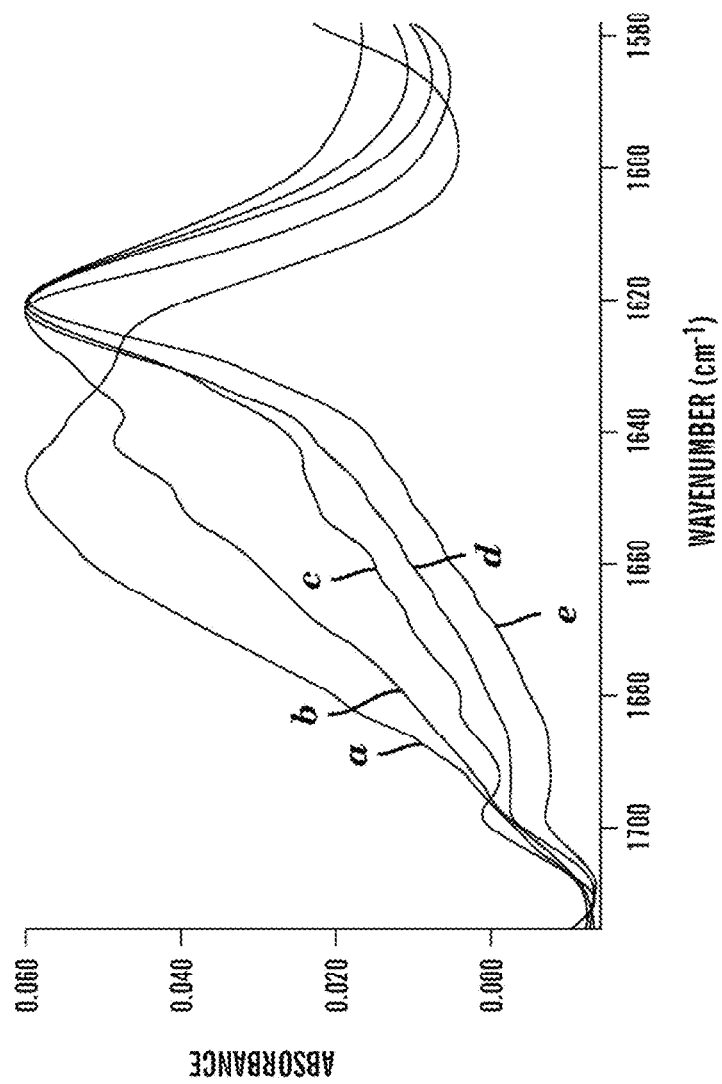
FIG. 5 represents FTIR spectra (amide I band) of silk microspheres prepared (a) as lyophilized DOPC-silk suspended in water; (b), (c), and (e) as silk microspheres prepared with 1, 4, and 15 h NaCl treatment and suspended in water, respectively; and (d) as silk microspheres prepared with MeOH treatment.

The β-sheet content in the MeOH- and NaCl-based microspheres was assessed by FTIR (FIG. 5). When the NaCl treatment time was increased, the absorbance at the region of random coil, α-helix, and turn and bend (1640-1690 cm$^{-1}$) significantly decreased (curve b, c, e in FIG. 5), indicating that the β-sheet structure (silk II band at characteristic region (1620-1630 cm$^{-1}$)) was increasing. Deconvolution of the curves showed that the initial material, freeze-thawed and lyophilized DOPC-silk, contained about 29% β-sheet structure, which is slightly higher than the 25% content that has been reported for soluble silk fibroin in an aqueous solution. This indicates that the protein structure was not significantly influenced by the freeze-thaw and lyophilization process under the experimental condition (mixed with lipids). The NaCl-based microspheres with 1 h, 4 h, and 15 h NaCl treatment showed β-sheet contents of about 34%, 51%, and 67%, respectively. MeOH-based microspheres also showed high β-sheet content of about 58%. These trends indicate that the β-sheet content in silk microspheres increases as the micropshere size decreases.

Controlled Drug Release

1. Silk and Drug Distribution in Silk Microspheres

The distribution of fluorescein-labeled silk (green) and rhodamine B labeled dextran 40,000 (red) in microspheres

TABLE 1

| Characteristics of silk microspheres | | | | | | | |
|---|---|---|---|---|---|---|---|
| | DOPC-silk | DOPC-silk MeOH | DOPC-silk Freeze-thaw | MeOH-based MS | 1 h NaCl MS | 4 h NaCl MS | 15 h NaCl MS |
| Particle Size (μm)[1] (mean ± SD) n = 3 | — | — | — | 1.73 ± 0.11 | 2.70 ± 0.35 | 2.24 ± 0.17 | 1.60 ± 0.09 |
| Phospholipids content[2] (%) | — | — | — | 0.965 ± 0.16 | — | — | 17.13 ± 2.14 |
| HRP loading[3] (ug/mg silk MS) | 0.082 ± 0.006 | 0.086 ± 0.013 | 0.165 ± 0.012 | 0.173 ± 0.02 | 0.062 ± 0.007 | 0.109 ± 0.013 | 0.148 ± 0.019 |
| HRP Loading efficiency[4] (%) | 9.8 ± 0.7 | 9.6 ± 1.4 | 19.8 ± 1.4 | 20.8 ± 2.4 | 7.4 ± 0.8 | 13.1 ± 1.6 | 17.8 ± 2.2 |

Figure 6A:
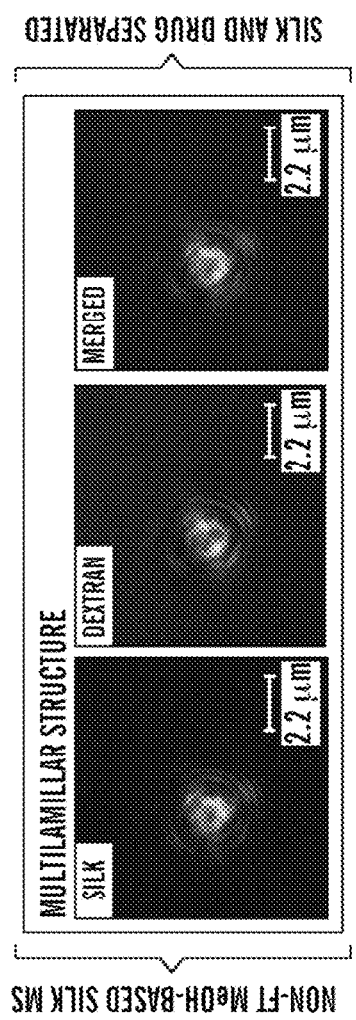
FIG. 6 depicts confocal laser scanning microscopy images showing the distribution of silk and drug in silk microspheres. Fluorescein-labeled silk (left panels) and rhodamin B-labeled dextran 40,000 (middle panels) are located in separate layers (A) or domains (B) in MeOH-based microspheres prepared from lyophilized DOPC, silk, and drug mixture. The same mixture when freeze-thawed prior to lyophilization shows that the silk and drug are mixed in the same layers (C) and domains (D) in both MeOH-based and NaCl-based microspheres. Images in the left and middle panels are merged into the right panels. Bar indicates 5.29, 1.49, 2.24, and 3.67 µm in A, B, C and D, respectively.
Figure 6B:
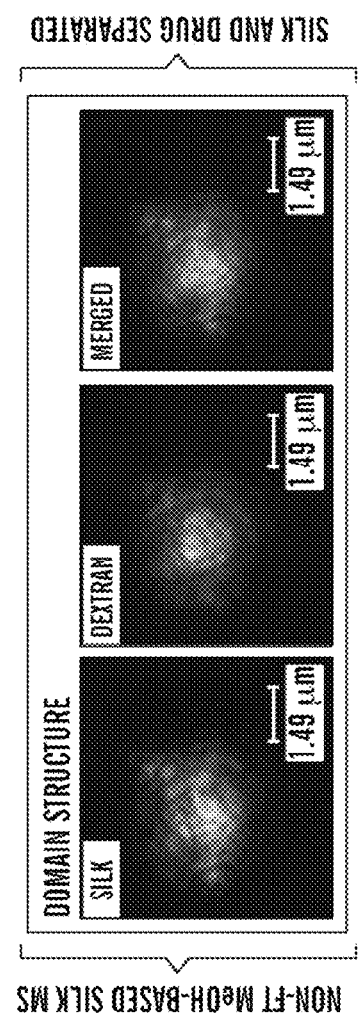

[1]Determined by dynamic lighter scattering. Standard deviation (SD) obtained based on three measurements.
[2]Phospholipids content represents the weight percentage of phospholipids in microspheres.
[3]Determined by directly mixing substrate TMB with the microspheres suspended in buffer.
[4]Calculated by comparing the amount of HRP determined in the silk microspheres with the total amount of HRP added at the beginning.

was studied by confocal laser scanning microscopy. When the freeze-thaw step was not included in the preparation, silk and dextran were found to locate in separate layers (FIG. 6A) or domains (FIG. 6B) in the MeOH-based microspheres. Once the freeze-thaw treatment was performed before lyophilization, in both MeOH- and NaCl-based microspheres, the silk and dextran were mixed in the layers (FIG. 6 C, D). Freeze-thaw was used to promote mixing between the silk fibroin and the rhodamine B-labeled dextran 40,000.

2. HRP Loading in Silk Microspheres

Loading was determined in lyophilized DOPC-silk with and without freeze-thaw. The freeze-thaw step increased the loading and loading efficiency by approximately two-fold when compared to the non-freeze-thawed samples (first and third columns in Table 1). This might be because the freeze-thaw treatment helped mix silk and drug in the microspheres so that more drug molecules could be packed into the microspheres. MeOH treatment on both samples did not deactivate the HRP and, therefore, the loading and loading efficiency were not changed in the corresponding MeOH-based microspheres (first and second, third and fourth, columns in Table 1). The loading and loading efficiency in the NaCl-based microspheres with 1 h treatment were much lower than those in the original material (third and fifth columns in Table 1), but increased with time of NaCl treatment. The 15 h treatment led to the loading of about 0.15 µg of HRP per mg of silk microspheres, close to the level in the original material (third and last columns in Table 1). It is likely that some empty lipid vesicles that were not yet fused after shorter NaCl treatments were co-precipitated with silk microspheres, which contributed to the measured weights and lowered the loading as a result.

3. HRP Release from Silk Microspheres

Figure 7A:
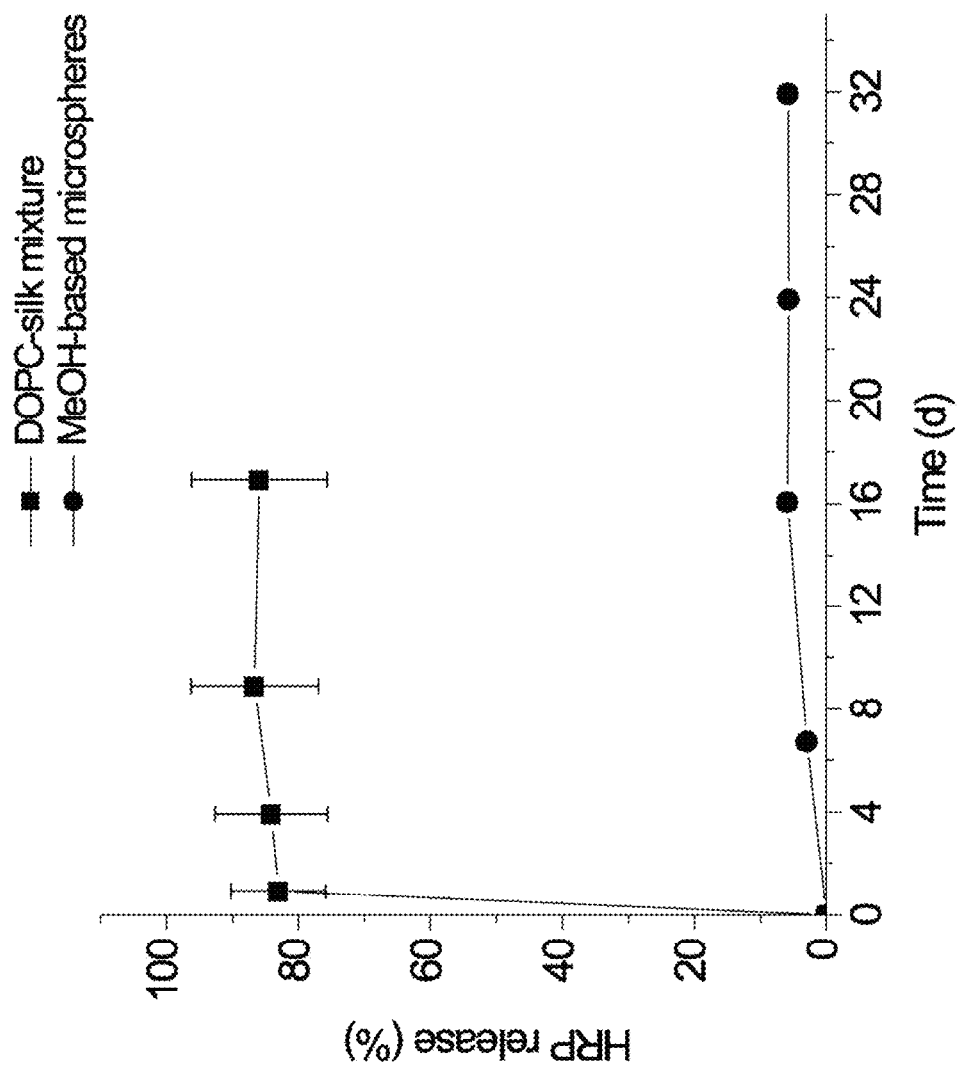
FIG. 7 represents (A) the HRP release from MeOH-based silk microspheres (●) and DOPC-silk mixture prior to MeOH treatment (■) and (B) the HRP release from NaCl-based silk microspheres after NaCl treatment for 1 h (■), 4 h (●), and 15 h (▲). Error bars represent standard deviations from samples n=3.
Figure 7B:
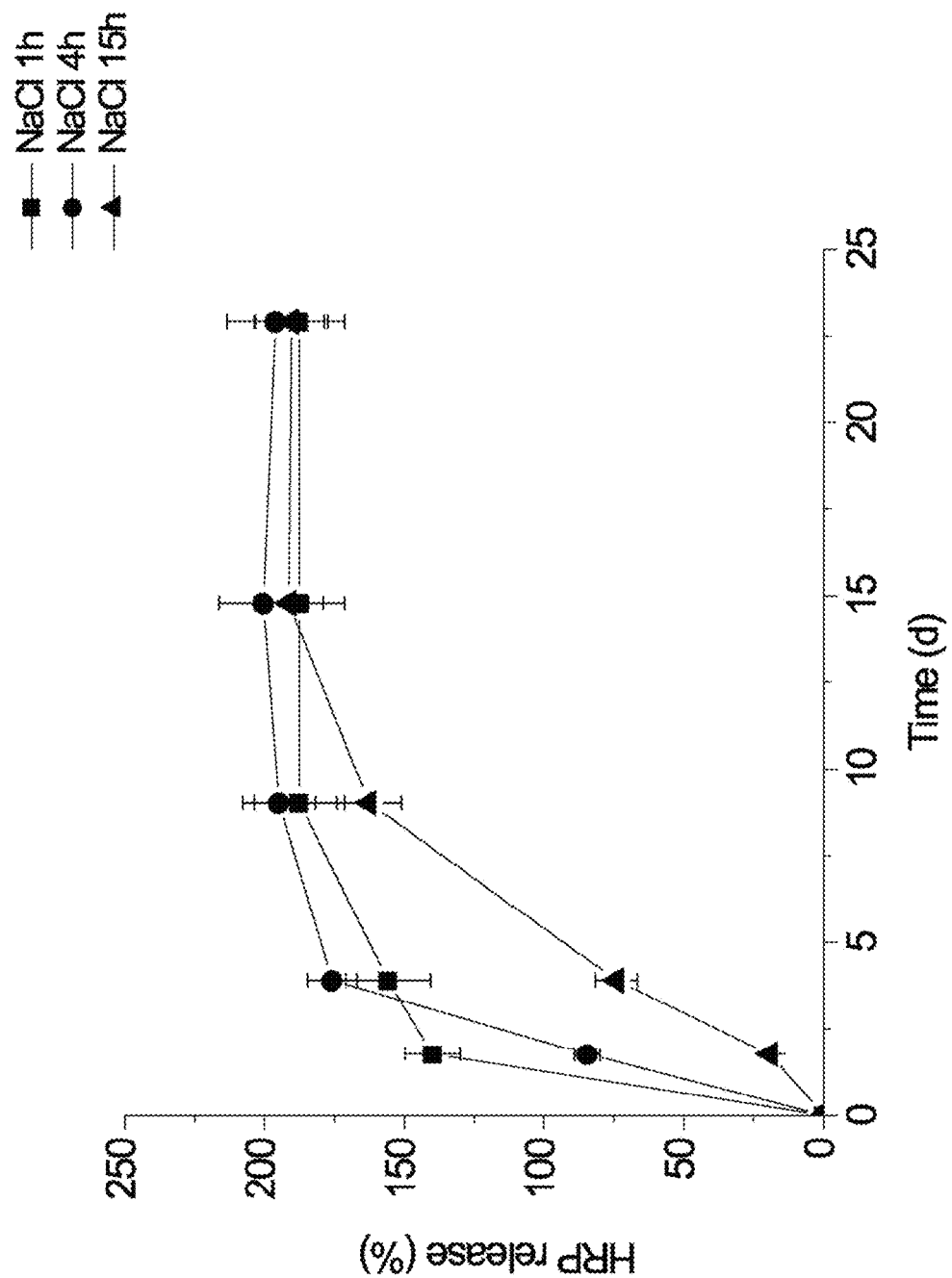
Figure 8:
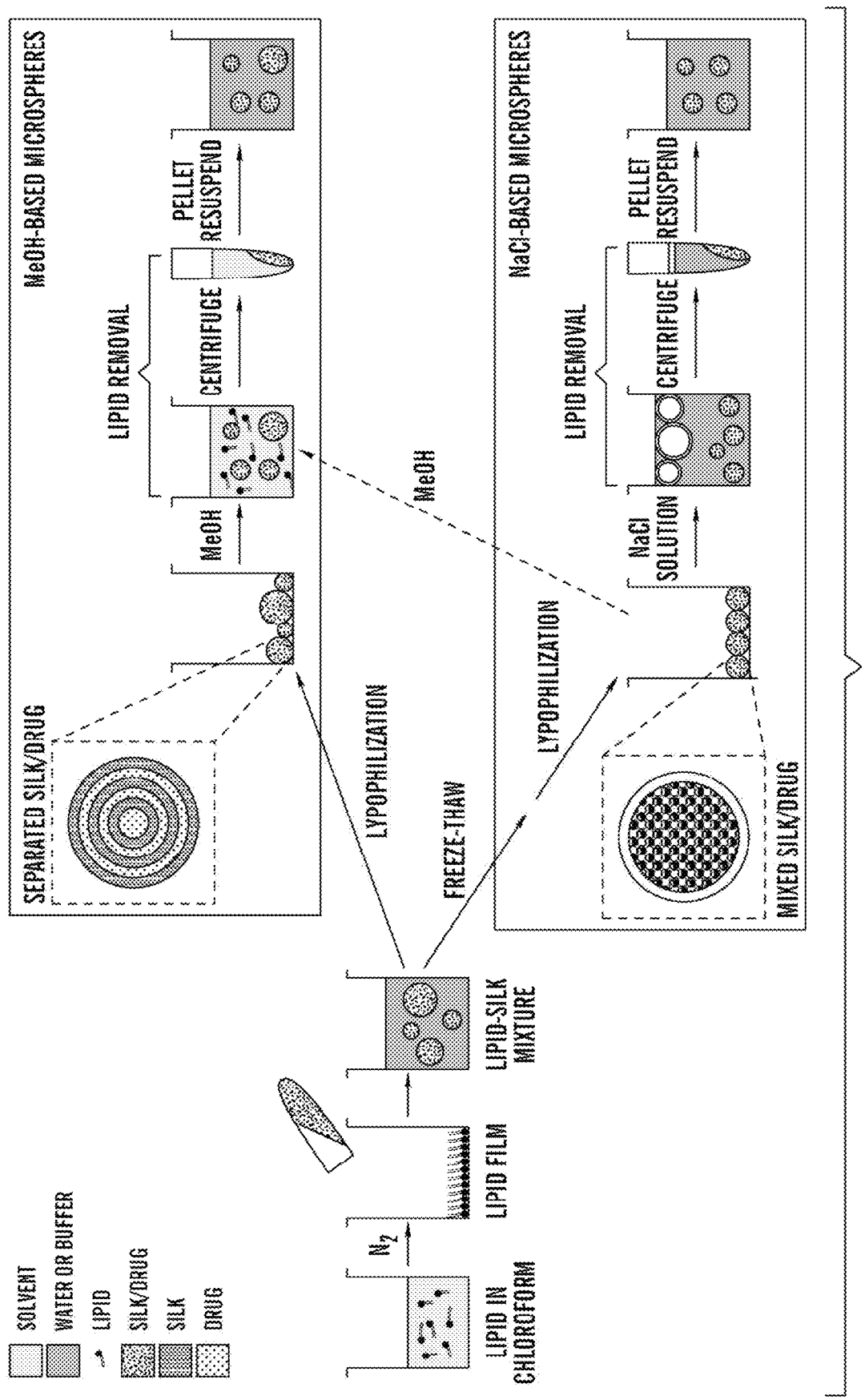
FIG. 8 represents a schematic showing the process of preparing MeOH-based and NaCl-based microspheres.

HRP that was encapsulated in lyophilized DOPC-silk displayed a significant release once the material was suspended in PBS buffer (FIG. 7A). In contrast, less than 5% HRP was released from the MeOH-based microspheres (with or without freeze-thaw treatment) into the surrounding buffer over a period of one month (FIG. 7A). The activity in the microspheres, however, dropped slowly, with about 50% remaining after one month (data not shown). NaCl-based microspheres released encapsulated HRP at different release rates, depending on the NaCl treatment time used. When the treatment lasted for 15 h, a sustained release which reached maximal level after 15 days was achieved (FIG. 7B). The 1 h and 4 h treated samples released HRP more quickly. For all these three samples, the HRP release reached about 200%. It is known that HRP activity can be inhibited by many factors, including metal ions like $Mn^{2+}$, $Co^{2+}$, $Ni^{2+}$, and $Cu^{2+}$, L-cystine and sulfide, and surfactants and lipids. Therefore, it is likely that some of these factors within the microspheres inhibited certain HRP activity, resulting in an underestimation of HRP loading (Table 1). Once released to the buffer, the inhibited HRP activity was restored.

The HRP release as calculated by dividing the amount of release by the loading, which produced values higher than 100%. It is hard to determine the absolute HRP loading in this case since it is difficult to extract HRP from silk microspheres while keeping the enzyme active. NaCl treatment induces the formation of β-sheet structures, as demonstrated in FIG. 5, with beta sheet content dependent on time of treatment, which produced different drug release profiles.

The encapsulated HRP was released slower from MeOH-based microspheres as compared to NaCl-based microspheres with 15 h treatment, despite the fact that their β-sheet contents were both high (58% and 67%, respectively). The discrepancy might be due to the different amount of phospholipids in MeOH-based microspheres (1%) and NaCl-based microspheres (17%). It is believed that having more phospholipids in microspheres provided more channels for HRP to escape.

Because of its excellent entrapment capability, MeOH-based silk microspheres are the preferred long-term drug delivery and enzyme immobilizations. It is believed that other alcohol- or solvent-based silk microspheres, such as ethanol, propanol, acetone, chloroform, or polyethylene glycol solutions, would provide similar entrapment capabilities for drug delivery. Because of its mild preparation condition and controllable crystalline β-sheet structure formation, NaCl-based microspheres are the preferred microspheres for those applications in which protein drugs or other therapeutic drugs are susceptible to methanol or alcohol treatment alternative drug release kinetics are needed. It is believed that other salt-based silk microspheres, such as potassium chloride, would also be suitable for these applications.

The silk microspheres may also be used for tissue engineering applications. For instance, by combining silk scaffolds with the microspheres, the system can be used to deliver growth factors in a time- and/or spatial-controllable manner so that the artificial tissues like bone and cartilage can be generated with more localized control from these scaffolds. Depending on the processing, MeOH-based and NaCl-based silk microspheres released encapsulated HRP with different kinetics, suggesting that the silk microspheres can be useful and can carry sufficient growth factors for tissue engineering applications.

Aside from controlled drug delivery, silk microspheres can also be used to immobilize enzymes for biosensor purposes. For instance, by combining silk microspheres and layer-by-layer coating techniques using silk fibroin, enzyme-based electrodes can be envisioned for use in a variety of applications, such as in the food industry, environmental control, and biomedical applications.

We claim:

1. A pharmaceutical formulation comprising silk fibroin microspheres, wherein the silk fibroin microspheres are produced by a method comprising:
   a) mixing a silk fibroin solution with a lipid composition, wherein the silk fibroin solution contains at least one therapeutic agent;
   b) lyophilizing the mixture;
   c) combining the lyophilized material with a dehydration medium for a sufficient period of time to at least partially dehydrate the silk fibroin solution and induce β-sheet structures in the silk fibroin; and
   d) removing at least a portion of the lipids to form silk fibroin microspheres, wherein the therapeutic agent is encapsulated in the silk fibroin microspheres, and wherein at least 75% of the microspheres are spherical or substantially spherical, and wherein the microspheres have a smooth surface morphology.

2. The formulation of claim 1, wherein the average size of the microspheres is less than 2.0 µm.

3. The pharmaceutical formulation of claim 1, wherein the microspheres contain about 1 to about 25% of lipid components by weight.

4. The pharmaceutical formulation of claim 1, wherein the lipid components are selected from the group consisting of 1,2-dioleoyl-sn-glycero-3-phosphocholine (DOPC); 1,2-dioleoyl-sn-glycero-3-phosphoethanolamine (DOPE); 1,2-dilauroyl-sn-glycero-3-phosphocholine (DLPC); and 1,2-dimyristoyl-sn-glycero-3-phosphocholine (DMPC).

5. The pharmaceutical formulation of claim 1, wherein the therapeutic agent is selected from the group consisting of proteins, peptides, nucleic acids, peptide nucleic acids, aptamers, antibodies, growth factors, cytokines, enzymes, small molecules, and combinations thereof.

6. The pharmaceutical formulation of claim 1, wherein the therapeutic agent is selected from the group consisting of morphogenetic protein 2 (BMP-2), insulin-like growth factor I and II (IGF-I and II), epidermal growth factor (EGF), platelet-derived growth factor (PDGF), fibroblast growth factors (FGFs), transforming growth factors-β (TGFs-β), transforming growth factors-α, erythropoietin (EPO), interferon α and γ, interleukins, tumor necrosis factor α and β, insulin, antibiotics, adenosine, and combinations thereof.

7. The pharmaceutical formulation of claim 1, wherein at least 75% of the microspheres have a diameter ranging from about 1 to about 3 microns.

8. The pharmaceutical formulation of claim 1, wherein the silk fibroin and the therapeutic agent are located in separate layers or domains of the microspheres.

9. The pharmaceutical formulation of claim 1, wherein the lipids in the silk fibroin microspheres forms unilamellar or multilamellar structures.

10. A drug delivery composition comprising a therapeutic agent encapsulated in crosslinked silk fibroin microspheres, wherein the microspheres comprise:
 lipid components in an amount no greater than 20% of the microspheres by weight; and
 silk fibroin, 50% or more of which is in β-sheet form, wherein the lipid components are integrated with the silk fibroin.

11. The composition of claim 10, wherein the therapeutic agent is released in a controlled-release manner from the microspheres.

12. The composition of claim 10, wherein the microspheres contain less than 5% lipid components by weight.

13. The composition of claim 10, wherein the weight percentage of the microspheres that is silk fibroin is at least 50%.

14. The composition of claim 10, wherein the average size of the microspheres is less than 2.0 μm.

15. The composition of claim 10, wherein the crosslinking of the silk fibroin microspheres was induced by exposing the silk fibroin to methanol or sodium chloride.

16. The composition of claim 10, wherein the lipid components are selected from the group consisting of 1,2-dioleoyl-sn-glycero-3-phosphocholine (DOPC); 1,2-dioleoyl-sn-glycero-3-phosphoethanolamine (DOPE); 1,2-dilauroyl-sn-glycero-3-phosphocholine (DLPC); 1,2-dimyristoyl-sn-glycero-3-phosphocholine (DMPC); and combinations thereof.

17. The composition of claim 10, wherein the therapeutic agent is selected from the group consisting of proteins, peptides, nucleic acids, peptide nucleic acids, aptamers, antibodies, growth factors, cytokines, enzymes, small molecules, and combinations thereof.

18. The composition of claim 10, wherein the therapeutic agent is selected from the group consisting of morphogenetic protein 2 (BMP-2), insulin-like growth factor I and II (IGF-I and II), epidermal growth factor (EGF), platelet-derived growth factor (PDGF), fibroblast growth factors (FGFs), transforming growth factors-β (TGFs-β), transforming growth factors-α, erythropoietin (EPO), interferon α and γ, interleukins, tumor necrosis factor α and β, insulin, antibiotics, adenosine, and combinations thereof.

19. The composition of claim 10, wherein at least 75% of the microspheres have a diameter ranging from about 1 to about 3 microns.

20. The composition of claim 10, wherein the silk fibroin and the therapeutic agent are located in separate layers or domains.

21. The composition of claim 10, wherein the lipid components in the silk fibroin microspheres form unilamellar or multilamellar structures.

22. A method of preparing silk fibroin microspheres, the method comprising:
 a) providing a silk fibroin-lipid mixture;
 b) lyophilizing the silk fibroin-lipid mixture;
 c) combining the lyophilized silk fibroin-lipid mixture with a dehydration medium for a sufficient period of time to at least partially induce β-sheet structures in the silk fibroin; and
 d) removing at least a portion of the lipids to form silk fibroin microspheres.

23. The method of claim 22, wherein the method further comprises freeze-thawing the silk fibroin-lipid mixture prior to lyophilizing.

24. The method of claim 22, wherein the dehydration medium comprises methanol or NaCl.

25. The composition of claim 10, wherein at least 75% of the microspheres are spherical or substantially spherical.

26. The composition of claim 10, wherein the microspheres have a smooth surface morphology.

* * * * *